United States Patent [19]

Maher

[11] Patent Number: 5,103,814
[45] Date of Patent: Apr. 14, 1992

[54] SELF-COMPENSATING PATIENT RESPIRATOR

[76] Inventor: Timothy Maher, 5266 Sharp Blvd., Mandeville, La. 70448

[21] Appl. No.: 398,324

[22] Filed: Aug. 24, 1989

Related U.S. Application Data

[63] Continuation of Ser. No. 187,505, Apr. 28, 1988, abandoned.

[51] Int. Cl.⁵ ............................................. A61M 16/00
[52] U.S. Cl. .......................... 128/204.18; 128/204.23; 128/205.11
[58] Field of Search .................... 128/716, 719, 204.18, 128/204.21, 204.22, 204.23, 205.11

[56] References Cited

U.S. PATENT DOCUMENTS 4,326,513  4/1982  Schulz et al. ................. 128/204.23
4,653,498  3/1987  New, Jr. et al. ................. 128/633

OTHER PUBLICATIONS

"Apparatus for the Servocontrol of Arterial Oxygen Tension in Preterm Infants", Medical & Biological Engineering & Computing, Jul. 1979, pp. 449–452, by Collins et al.
"An Optimally Controlled Respirator", IEEE Transactions on Bio-Medical Engineering, vol. BME-18, #5, Sep. 87, by Mitamura et al.

Primary Examiner—Edgar S. Burr
Assistant Examiner—Aaron J. Lewis
Attorney, Agent, or Firm—Alexander F. Norcross

[57] ABSTRACT

A ventilator has automatic controls with a particular control sequence to progressively wean the patient from mechanical ventilation, but that detects and maintains the patient's condition against the patient's inability to resume normal respiration. The ventilator non-invasively monitors body oxygen saturation level to insure adequate respiration, with minimum excess oxygen exposure, and monitors exhaled tidal carbon dioxide levels to control mechanically assisted respiration rate.

6 Claims, 1 Drawing Sheet

SELF-COMPENSATING PATIENT RESPIRATOR

This is a continuation of application Ser. No. 07/187,505 filed on Apr. 28, 1988, now abandoned.

BACKGROUND OF THE INVENTION

This invention relates to respirators, for the ventilation of persons whose normal respiratory function is impaired.

Ventilators, or respirators, in medical practice are machines designed to assist a respiratorily impaired patient with breathing. Breathing is a complicated physiological process, but in simplified form, it is a means of delivering oxygen while simultaneously removing carbon dioxide from the tissues of the body.

This is accomplished by the interrelationship of the lungs and by blood circulation; oxygen being transported primarily in bound form in hemoglobin within the blood, and carbon dioxide being primarily transported in solution form in blood plasma.

The most exact indication of proper ventilation is obtained through means of blood gas studies, which can accurately indicate the dissolved and transported oxygen and carbon dioxide within the patient's blood. Since both oxygen and carbon dioxide are ultimately transported across tissue interfaces by diffusion, the partial pressures of the gasses in the solution are the most important criteria, as these indicate whether adequate flow of oxygen and carbon dioxide is occurring.

In a respiratorily impaired patient, a mechanical ventilator is used to augment the breathing process. With current ventilators and modern day medical practice, a number of variables are routinely controlled in order to achieve adequate ventilation of the patient. Primarily controlled variables include the percentage of oxygen in the gas delivered to the respiratory patient's lungs, the number of breaths per minute delivered to the patient, and the tidal volume or total volume of air interchanged in each delivered breath.

Secondary variables which are important in specific patients include positive end expiratory pressure (PEEP), the time of inspiration and expiration with relation to the overall cycle of the breath and the peak flow rate of gas being delivered during a breath. These latter variables may be controlled by a physician as required to overcome certain disease or injury related processes or degradations of the lungs.

When the patient is placed on a ventilator, positive gas passing to the lungs is provided either by an inserted endotracheal tube or, in some cases, by means of a tracheotomy. Depending upon the condition of the patient, various of the above controlled variables are set, the most important being the percentage of oxygen within the respiratory gas to be delivered, the number of breaths per minute to be delivered, the volume of each breath, and the amount of pressure to be maintained in the lungs after expiration (PEEP). After a patient is placed on a ventilator, there are two major goals in his treatment: the first is to decrease the percentage of oxygen in delivered gas to an acceptable partial pressure, as high oxygen percentages over a long period of time are toxic to the lungs; the second is to allow the patient to breathe for himself as much as possible, decreasing the actual mechanical breathing performed by the ventilator.

Various prior art sensors and control combinations have been suggested. Thus, Schultz, U.S. Pat. No. 4,326,513, suggests a control system within a respirator, using a sensor to directly measure the arterial partial pressure of oxygen which, in a closed loop through a mixer, mixes oxygen with other breathing gasses so as to minimize the oxygen concentration while maintaining a desired arterial oxygen partial pressure. This is limited, however, by the lack of a suitably accurate, medically approved, real time sensor for arterial partial pressure of oxygen.

U.S. Pat. No. 3,734,091 to Taplin discloses the use of a device to detect super-saturation of oxygen in the body, together with a control device which produces a temporarily anoxic (oxygen deficient) status within the user to control the oxygen concentration in the breathing mixture. The device is described as being used to maintain close to one hundred percent saturation of oxygen within the body, but is unusable in a respiratorily inhibited patient as the deliberate induction of an anoxic state in such a patient is extremely hazardous.

Separately, a number of patents have used $CO_2$ analysis of exhaled gas to start and stop respirator action. U.S. Pat. No. 4,537,190 to Caillot discloses the use of a $CO_2$ analysis cell within the exhaled air together with a control unit which turns the respirator on or off depending upon the level of exhaled $CO_2$ detected.

U.S. Pat. No. 4,617,924 discloses a particular $CO_2$ detection and controller of use in a high frequency ventilation system, disclosing an adaptation to permit final expiratory $CO_2$ concentration to be more accurately determined when the exhaled gas may be intermingled with flush gas, to alleviate an inaccuracy otherwise inherent in high frequency ventilation systems, due to the dilution of the exhaled gasses by flush gas flow.

U.S. Pat. No. 4,016,876 to Martin discloses a breathing apparatus for a healthy user, particularly a fire fighter's breathing system, in which the amount of exhaled carbon dioxide is utilized to trigger replenishment within an air re-breathing apparatus. The device is suitable solely for control of closed cycle respirators for use by otherwise healthy personnel.

A similar, constant volume re-breathing system is shown in U.S. Pat. No. 3,951,137 to Conkle, which utilizes detection of differential pressure, by measuring the inhalation and exhalation pressure induced by respiration of the user to trigger a following effect in the respirator-breathing apparatus.

U.S. Pat. No. 4,612,928 to Tiep discloses a method of minimizing utilization of oxygen within an oxygen rebreather by using a pulse detection circuit to detect breathing cycles in the individual and by supplying oxygen only during inhalation steps.

Sensors for the monitoring of exhaled gasses are shown in U.S. Pat. No. 4,631,966 to Brugnoli and U.S. Pat. No. 4,602,653 to Ruiz-Vela.

SUMMARY OF THE INVENTION

A ventilator is shown, having automatic controls with a particular control sequence, providing a ventilator which progressively weans the patient from the necessity for mechanical ventilation, where this is possible, but that detects and maintains the patient's condition against an inability of the patient to resume normal respiration.

The ventilator utilizes sensors of proven reliability, and has a control sequence which is adapted to the particular form of the sensor concerned to insure the patient's safety, and to insure proper ventilator functioning.

The ventilator of this design progressively controls two of the major ventilator functions; percentage of oxygen in the respirated gas, and the total amount of assisted ventilation (the number of breaths per minute). Other variables, such as tidal volume of gas respirated per breath, positive end expiratory pressure, and the like, need not be automatically varied for proper respirative function, but may be set based upon the patient's physical condition and disease state at the beginning of ventilation.

The patient's respiration status is non-invasively monitored to control the patient's blood oxygen level and to determine that adequate respiration is taking effect.

No direct, non-invasive blood gas measurement techniques exist. This inventive ventilator therefore provides a particular control mechanism based upon the indirect monitoring of these psychological effects related to critical variables. Blood oxygen is controlled by ascertaining, through the use of a prior art pulse oximeter, the degree of the total body oxygen saturation. A blood oximeter is a device, well developed and known, which utilizes a light probe which measures the patient's pulse through a thin area of the skin, such as a finger or ear lobe, and in turn is able to adequately sense oxygen saturation within the patient.

Oxygen saturation is not a linear function of blood oxygen partial pressure, but is related through a complex second order relationship which reflects essentially the sensitivity of blood transport of oxygen to the minimum blood partial pressure necessary to provide for binding of oxygen to blood hemoglobin.

Blood carbon dioxide can likewise be estimated by monitoring the overall carbon dioxide level in the exhaled breath of the patient, or the end tidal $CO_2$; again, this is an indirect measurement of overall partial pressure of carbon dioxide in the blood, representing as it does, a measure of the transport of carbon dioxide across the lungs, due to differential partial pressure of carbon dioxide between the blood and the lungs.

The inventive ventilator therefore utilizes the body $O_2$ saturation level, as detected by a pulse oximeter, and the exhaled $CO_2$ percentage as detected by an end tidal $CO_2$ monitor to control the ventilator for a given patient to automatically adjust the ventilator to deliver correct inspired oxygen and the correct number of breaths per minute, all the while progressively weaning the patient, to the extent possible, from the necessity for mechanical ventilation, by weaning the patient down to the lowest acceptable inspired oxygen level as well as to decrease the number of breaths mechanically delivered to the patient to the lowest extent tolerable to the patient.

In order to insure that the machine is properly set up for an individual patient, and to properly calibrate the machine to the patient, an initial blood gas is taken for a given patient to determine the existing oxygen and carbon dioxide blood gas levels. Based upon this, an initial setting of all relevant parameters for the ventilation will be made based on normal medical indicia. Additionally, the machine will be set to a specified minimally acceptable oxygen saturation and to a maximally acceptable carbon dioxide level. A minimum respiratory gas oxygen percentage will be set, typically at forty to fifty percent inspired oxygen, but in any case, below the level at which long term oxygen toxicity effects occur.

The ventilator then is controlled progressively by an interrelated series of step decrease functions which act as follows.

First, the inspired oxygen percentage is decreased by fixed step amount, typically ten percent. For a period of time, the patient's oxygen saturation is monitored to determine whether it has dropped below the minimum level set point, picked to insure adequate minimum blood partial pressure of oxygen, and therefore typically at least ninety percent saturation.

If the oxygen saturation of the patient has not dropped below the minimum acceptable level, then the ventilator breath rate will be decreased by a step amount and the exhaled $CO_2$ level monitored. Again, there is a sensible time delay between this change and stabilization of the exhaled $CO_2$ at the new level. Provided that the exhaled $CO_2$ level runs at or below the maximally acceptable $CO_2$ levels set for the particular patient, reflecting the relationship between that patient's exhaled $CO_2$ and the initial blood gas level determined for that patient upon start of ventilation, then the ventilation rate will be maintained at the new lower level and the process repeated.

For most patients the process will progress until the oxygen level has been reduced to the minimum level and the ventilation assisted breath rate has been decreased to zero, indicating that the patient is breathing on his own, in a normal manner. If, however, at any point during the process either the oxygen saturation rate decreases below the acceptable amount or the exhaled $CO_2$ increases above the maximally accepted amount, then the ventilator will step back to the previous, higher rate and further decreases in that function will not occur.

Use of the innovative ventilator permits a safe coordinated weaning of a patient from mechanical ventilation without recurrent invasive blood gas tests and without requiring medical intervention at each progressive resetting of the ventilator while preserving at all times effective ventilation of the patient.

The invention also avoids instability problems in the prior art occasioned by failure to monitor both of the critical parameters necessary for insuring adequate ventilation, or by attempting to maintain a continuous control level while using sensors which are inherently incapable of directly measuring the essential parameter to be controlled.

DETAILED DESCRIPTION OF THE PREFERRED EMBODIMENT

Figure 1:
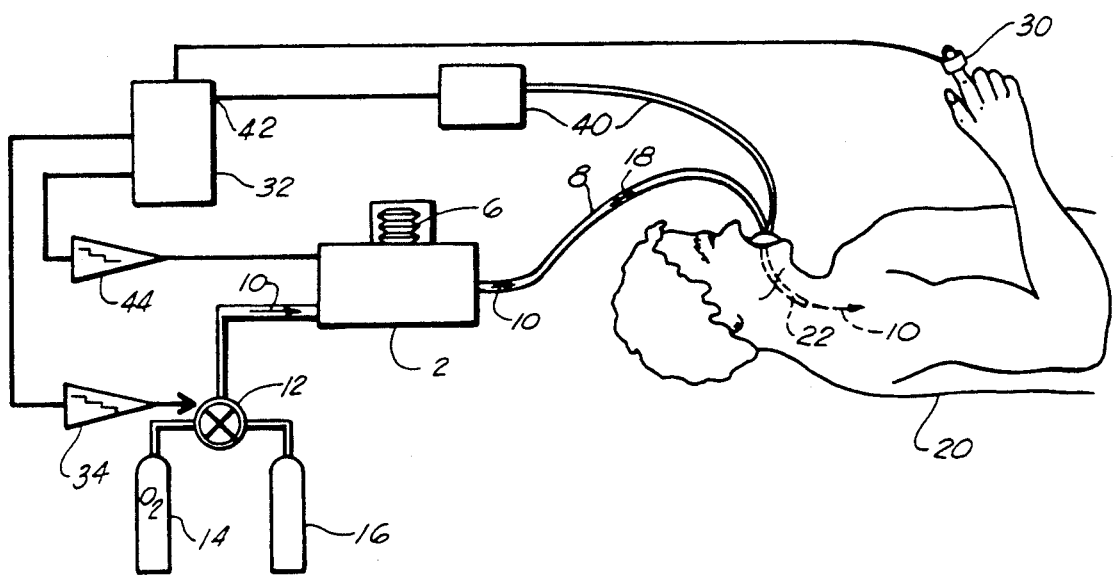
FIG. 1 is a block diagram of the invention in simplified form interconnected to a patient.

FIG. 1 shows, in block diagram form, the control system of the inventive ventilator herein described. A mechanical ventilator 2 provides a physical ventilation of a patient 20 through use of a mechanical respiratory gas pumping means 6. Respiratory means 6, a relatively large displacement, low pressure air pump, pumps periodic volumes of respiratory gas 10 through a flow means or tubing 8 to the patient 20. The gas is forcibly inspirated into the patient, typically through an endotracheal tube 22 providing direct forced respiration into the lungs 26 of the patient.

The respiratory gas 10 is a mixture of oxygen and other inert gasses in a proportion controlled for the ventilator 2 by setting an interval variable mixing means 12, which mixes controlled portions of oxygen 14 and other inert gasses 16 to proved the basic respiratory gas.

The pumping means 6 provides for a breathing pressure into the lungs 26 of the patient and a second, end respiratory pressure permitting the patient to exhale through exhalation gas flow 18.

The above mechanism is well understood in the art. In practice, such a ventilator 2 will have control means which will vary the pumping rate of the respiratory pumping means 6 so as to control typically the respiratory or breathing rate in breaths per minute, the maximum respiratory pressure during the inspiration stage, as well as the positive end expiratory pressure (PEEP), the specific timing of inspiration and expiration, the total tidal volume, as well as the peak flow rate of the respiratory gas to be delivered, and the percentage of oxygen in the gas, which establishes the partial pressure of oxygen in the breathing mixture at the lung-body interface.

When a patient 20 is placed upon a ventilator 2, gas flow is through endotracheal tube 22 placed in the patient's trachea, reaching from outside his mouth and nose, or alternatively implanted through a tracheotomy.

A blood gas test on the patient establishes the patient's initial level of blood oxygen partial pressure as well as the patient's dissolved carbon dioxide level. Using readily available medical knowledge, the ventilator may then be initially set; the most important of settings will be the percentage of oxygen to be delivered in the respiratory gas (oxygen partial pressure); the number of breaths per minute delivered by the ventilator; the volume of each breath delivered; and the amount of pressure to be maintained on the lungs after expiration (PEEP).

In general, a patient requiring respiration is in an oxygen depleted state, and initial ventilation is at a very high oxygen percentage. Long term oxygen exposure at partial pressures or percentages above fifty percent oxygen is toxic. Therefore, there are two major goals in management of a patient on a respirator. The first is to reduce the oxygen percentage, where possible, to below fifty percent in order to avoid toxicity effects to the lungs; the second is to reduce the mechanical breathing by the ventilator so that the patient will resume breathing on his own; in other words, the patient should be weaned from the ventilator.

The control variables are therefore set for initial ventilation based on the patient's size, lung function, disease state and other variables known in the medical art. After the patient has been respirated for a period of time, a blood gas is taken; that is, a blood sample is drawn and standard laboratory tests are used to analyze oxygen and carbon dioxide partial pressure within the patient's blood. The oxygen partial pressure must be maintained at a minimum level in order to insure that adequate oxygen transport to the patient's tissues occurs; this is necessary to sustain life. It is, however, important that an excessive amount of oxygen not be delivered to the tissues in order to prevent toxic effects from oxygen poisoning.

Carbon dioxide partial pressure must be maintained below a maximum level in order to avoid toxic effects from excessive carbon dioxide and additionally, as carbon dioxide levels in the blood controls the patient's respiratory function, to prevent respiratory failure. The percentage of carbon dioxide in the blood is the most sensitive indicator of the overall respiration function in the patient.

Figure 2:
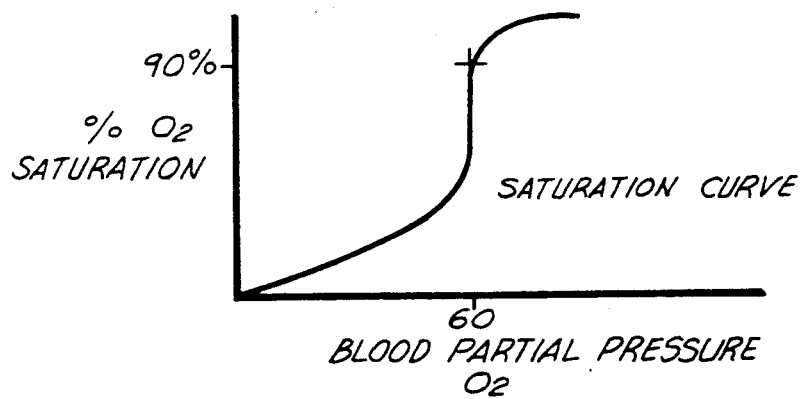
FIG. 2 is typical oxygen saturation curve showing the relationship between measured oxygen saturation and actual arterial partial pressure of oxygen.

In the inventive ventilator, the patient is coupled to a provided pulse oximeter 30 which is placed upon a thin extremity, such as a finger tip or ear lobe of the patient, and which by means of light transmission, measures the overall body saturation of oxygen. Referring to FIG. 2, it should be seen that the percentage of oxygen saturated within the body is not a simple function of the blood oxygen partial pressure, but rather that the blood oxygen partial pressure rapidly increases above sixty torr for an oxygen saturation percentage of above ninety percent, but even more rapidly collapses at a point somewhat below sixty torr in terms of a decrease in body oxygen saturation. This sudden break in the curve if an effect of the hemoglobin transport mechanism, which retains oxygen at a relatively stable partial pressure until a relatively low saturation level is achieved at which point total oxygen partial pressure rapidly drops, and the patient becomes anoxic.

It should thus be apparent that a simple closed loop control based on percentage oxygen saturation is not sufficiently precise to control the blood oxygen partial pressure, as excursions above a certain percentage saturation level produce rapid and uncontrolled increases in blood oxygen partial pressure, whereas decreases below the given saturation level can rapidly lead to hypoxia, causing serious irreversible damage to the patient.

The physiological purpose of respiration is to provide adequate oxygen support to the tissues of the body, while effectively removing metabolic byproducts, especially carbon dioxide, from the tissues. Maintenance of an oxygen partial pressure only satisfies the first part of this respiratory function; it is also necessary to insure that adequate ventilation or flow of gas across the lungs occurs so as to eliminate the carbon dioxide. Additionally, it is necessary to maintain the carbon dioxide within a relatively narrow range in order for the patient's normal breathing synapses to properly function and for the patient to resume breathing where that is physiologically possible.

In a respiratorily inhibited patient, it is possible to have a patient who will be incapable of mechanically resuming breathing, but whose lung function is otherwise unimpaired and where oxygen transport will occur at normal gas pressure; this is the typical picture presented by a paralyzed patient with otherwise undamaged lungs.

It is equally possible to have a patient whose respiratory function is uninhibited but who, through disease process or lung damage, has a very low capability to transport oxygen successfully from the air to the blood. Thus, an automatic ventilator must control independently both the oxygen partial pressure and the overall respiratory flow function.

The inventive ventilator 2 provides for such a control where the sensors are indirect sensors, not directly measuring the parameters to be controlled and where the patient may be weaned where possible through the function of the ventilator.

In addition to the oximeter measuring a body oxygen saturation percentage, the ventilator is provided with an end tidal $CO_2$ sensor 40 located within the respiratory gas flow means 8 so as to sample $CO_2$ from exhaled respiratory gasses during the expiration portion of the overall respiratory cycle as controlled by the ventilator.

Again, this provides an indirect measure of the overall $CO_2$ level within the lungs, but, for a specific patient having some specific given degree of lung function, once the relationship between blood gas $CO_2$ partial pressure and expired or end tidal $CO_2$ percentage is established, monitoring of the $CO_2$ level can be correlated for that one point.

Therefore, the innovative ventilator 2 is provided with control means 32 which concurrently perform two tasks as follows:

Oximeter 30 measures a signal proportional to body oxygen saturation percentage. This signal is provided to Oxygen level comparison means within control means 32, which compares the measured percentage to a predetermined set point oxygen saturation percentage to determine if oxygen saturation is above said chosen minimum point level, typically chosen at about ninety percent. So long as said oxygen saturation level is maintained or exceeded, a periodic mixer control means 34 step decreases the proportion of oxygen 14 within the overall respiratory gas 6 by varying the setting of the respiratory gas mixer 12. Since any particular change in setting requires a sensible amount of time to take a physiological effect, based on the overall rate of transport of the revised oxygen mixture to the lungs through the blood stream to the tissues which are measured by the oximeter 30, the step decrease is followed by a delay function which is timed by control means 34 to allow the patient's condition to stabilize between each change. Oxygen percentage is in this manner decreased until a minimum desired setting of regulatory gas mixer 12, which may be set based on general medical considerations, is achieved or until level comparison 32 indicates that the overall body oxygen saturation percentage has decreased below the minimum set level. The latter event indicates physiological lung damage or an inability of the lungs to properly transport oxygen; the previous step decrease is then reversed and the oxygen percentage is maintained continuously at the next higher minimum step. In the inventive ventilator here described, this is accomplished without establishing an anoxic condition in the patient, as shown below.

Separately, mechanical respiratory assistance is reduced as follows. An end tidal $CO_2$ sensor 40 measures a percentage $CO_2$ in expired breathing gas which is compared to a pre-set maximum $CO_2$ percentage, derived for the specific patient and representing a maximum desired $CO_2$ blood percentage.

Basically, failure of patient self-respiration will be indicated by a rise above acceptable levels of blood dissolved carbon dioxide; this in turn will result in an increase in carbon dioxide within the exhaled gasses.

The end tidal $CO_2$ sensor therefore provides a signal proportionate to the percentage of the $CO_2$ in the exhaled gasses which is provided to $CO_2$ level comparison means within control 32 where it is compared against a set maximum $CO_2$ level. So long as end tidal $CO_2$ is below the maximal set point, $CO_2$ rate control 44 is step decreased, decreasing the breath rate of respirator 2 in terms of breaths per minute. A time delay is interposed between each step for stabilization of the patient's respiratory function and redetermination of a stable, new end tidal $CO_2$. This process continues until the patient is breathing totally without mechanical assistance, or until expired and tidal $CO_2$ exceeds the set point level. In the latter case, the previous step rate decrease is reversed, and the patient is held at the next higher mechanical breathing rate, representing the lowest assistance level achievable.

In use, the ventilator 2 would have the normal settings of the prior art respirator, but in addition, would have control settings for minimum body oxygen saturation and maximum end tidal $CO_2$ level, and an additional setting for minimum percentage oxygen delivered in the respirated gas, all as determined medically for a specific patient.

Either the oxygen saturation can be first decreased, or the patient may first be weaned from the ventilator, by reducing mechanical respiration. Control 32 therefore has a setting to initiate either $O_2$ reduction or breath rate reduction first; control 32 does not initiate the second function until the first has reached its end state, so as to prevent a too radical decrease in respiratory function in the patient.

In either case, at the end state of the second function, the patient is maintained in a steady state, with the minimum mechanical respiratory assistance feasible.

As an example, if a patient is initially placed in a one hundred percent oxygen level, then the ventilator control will monitor the oxygen saturation through the pulse oximeter reading. So long a the pulse oximeter shows an acceptable oxygen saturation, that is, a level greater than that preset, the ventilator control internally would decrease the amount of oxygen delivered by, as an example, ten percent at twenty minute intervals. At the end of each set period, if the controller comparison means determines that the oxygen saturation remains above the preset level, the ventilator will again decrease the inspired oxygen by the set step amount. This process will continue at the preset interval for as long as the patient's oxygen saturation remains above the level set as minimally acceptable for the patient's condition, decreasing ultimately to the minimum established percentage, typically forty to fifty percent inspired oxygen. If, during this period of step decrease, the patient's oxygen saturation falls below the pre-programmed level, then the ventilator control program will return to the previous higher percentage of oxygen at which an acceptable saturation level was achieved.

Additionally, even if the patient has been weaned in terms of mechanical respiration assistance, continuing monitoring of oxygen saturation level will permit increase of oxygen should a worsening of the patient's disease state cause the patient's oxygen saturation to fall below the acceptable level.

The process is superior to that of repeated blood gas monitoring. Referring to FIG. 2, it can be seen that a blood gas monitor which monitors oxygen partial pressure has a point of insensitivity at a critical region immediately below sixty torr oxygen partial pressure of the typical patient where major changes in the patient's oxygen saturation will occur with relatively little change in the blood gas partial pressure. At the lower end of this insensitivity region a sudden and catastrophic decrease in blood oxygen content occurs for relatively small oxygen changes. By contrast, the inventive ventilator 2, by monitoring the patient's body oxygen saturation level, can be set at an upper point of inflection in the curve shown in FIG. 2. This results in considerably increased sensitivity due to the marked decrease in oxygen saturation which occurs immediately prior to the critical decrease in blood gas level. Since the blood gas partial pressure is the critical parameter to be preserved, this closed loop monitoring technique in this invention readily detects an impending critical decrease in oxygen, yet preserves the patient from the deliberate induction of a anoxic state taught in the prior art. This monitoring and control, part of the invention, is therefore intrinsically much safer for a diseased or respiratorily inhibited patient.

Subsequent to the above oxygen decrease, the end tidal $CO_2$ monitor provides continuous readings on expired $CO_2$ levels which will be compared to a preset maximally acceptable $CO_2$, individually programmed for a specific patient based on initial blood gas reading upon inception of ventilation. The size and volume of each breath would be set as in a traditional ventilator. It is part of the invention that the patient may be safely weaned by progressive, timed step decreases in the breath rate, based on the comparison on the end tidal $CO_2$ reading to the maximally acceptable expired $CO_2$ level preset, without the necessity for further variation of flow rate or tidal volume. Thus, the ventilator is programmed to step decrease the number of breaths given per minute, pausing and monitoring to determine that the end tidal $CO_2$ does not exceed the maximum acceptable level pre-programmed. Typically, the step decrease would be on the order of two breaths per minute with a hold period between step decreases of thirty minutes to one hour. The decrease will continue until the patient is breathing completely on his own, and thus, the patient is able to eliminate $CO_2$ completely on his own, as evidenced by the end tidal $CO_2$ remaining below the maximum set point level. Alternately, the assistance rate will decrease to the point where the end tidal $CO_2$ remains at a normal level and will stay at that level with no further decreases.

As with the oxygen monitoring, the internal control continues to monitor end tidal $CO_2$ so that if it subsequently rises above the pre-set programmed maximum rate, the ventilator will automatically resume or increase the number of breaths until an acceptable rate is maintained. A setting will also be provided on the ventilator permitting the physician to establish a minimum number of breaths per minute below which the machine will not wean.

It is part of the invention that the control relationships as stated above permit the use of indirect sensors related to body oxygen saturation rate and to expired end tidal $CO_2$, both of which are significantly time delayed with respect to blood gas partial pressures, and yet provides adequate and accurate control of a ventilator for maintaining a patient's blood gas partial pressures at acceptable levels during artificial ventilation, while reducing artificially induced respiration to the maximum extent possible, consistent with a patient's condition.

It should thus be apparent that the invention is limited not to the specific examples above given but rather to the broader control methodology within a respirator as declared in the claims.

I claim:

1. A ventilator for respiration of a respiratorily inhibited patient comprising:
a respirator;
pulse oximeter means for determining the body oxygen saturation of a patient;
oxygen comparison means comparing said body oxygen saturation to a predetermined body oxygen saturation level to determine whether
said body oxygen saturation is greater than said predetermined body oxygen saturation level or said body oxygen saturation is lesser than said predetermined body saturation level;
means, coupled to said respirator, for periodically decreasing the percentage of oxygen in a respiratory gas within said ventilator while said body oxygen saturation is greater than said predetermined body oxygen saturation level;
means for sensing expired $CO_2$ levels;
$CO_2$ comparison means for comparison of said expired $CO_2$ levels to a preset maximal level;
$CO_2$ control means for periodically decreasing a rate of breath actuation of said respirator to a level below which said expired $CO_2$ levels exceed said preset maximal level;
said $CO_2$ control means acting sequentially but not concurrently with said oxygen control means to control said ventilator.

2. A ventilator according to claim 1 wherein said first comparison means predetermined saturation level is at or above an upper point of inflection of an oxygen saturation/oxygen blood partial pressure curve.

3. The ventilator of claim 1 wherein said first comparison means predetermined saturation level is above the level at which the patient exhibits an hypoxic condition.

4. A ventilator for respiration of a respiratorily inhibited patient comprising:
a respirator connected to a source of respiratory gas through an oxygen mixing regulator;
non-invasive means for externally determining the body oxygen saturation of a patient;
means for comparing said body oxygen saturation to a predetermined body oxygen saturation level;
means coupled to said oxygen mixing regulator for periodically decreasing the percentage of oxygen in said respiratory gas supplied to said respirator while said externally determined body oxygen saturation is greater than said predetermined body oxygen saturation level;
means for determining the expired carbon dioxide level of the patient;
means for controlling the breath rate of said respirator within said ventilator in response to the expired carbon dioxide level of the patient.

5. A ventilator according to claim 4 wherein said predetermined body oxygen saturation level is at or above an upper point of inflection of an oxygen saturation/oxygen blood partial pressure curve.

6. The ventilator of claim 4 wherein said predetermined body oxygen saturation level is above the level at which the patient exhibits in hypoxic condition.

* * * * *